US010280393B2

(12) United States Patent
Foustoukos

(10) Patent No.: US 10,280,393 B2
(45) Date of Patent: May 7, 2019

(54) HIGH PRESSURE BIOREACTOR

(71) Applicant: Carnegie Institution of Washington, Washington, DC (US)

(72) Inventor: Dionysis Ioannis Foustoukos, Washington, DC (US)

(73) Assignee: CARNEGIE INSTITUTION OF WASHINGTON, Washington, DC (US)

( * ) Notice: Subject to any disclaimer, the term of this patent is extended or adjusted under 35 U.S.C. 154(b) by 0 days.

(21) Appl. No.: 15/121,732

(22) PCT Filed: Feb. 27, 2015

(86) PCT No.: PCT/US2015/018004
§ 371 (c)(1),
(2) Date: Aug. 25, 2016

(87) PCT Pub. No.: WO2015/131046
PCT Pub. Date: Sep. 3, 2015

(65) Prior Publication Data
US 2017/0015972 A1    Jan. 19, 2017

Related U.S. Application Data

(60) Provisional application No. 61/946,057, filed on Feb. 28, 2014, provisional application No. 62/074,845, filed on Nov. 4, 2014.

(51) Int. Cl.
*C12M 1/34* (2006.01)
*C12M 1/02* (2006.01)
(Continued)

(52) U.S. Cl.
CPC ............ *C12M 41/40* (2013.01); *C12M 27/00* (2013.01); *C12M 29/00* (2013.01); *C12M 33/00* (2013.01)

(58) Field of Classification Search
CPC ...... C12M 27/00; C12M 29/00; C12M 33/00; C12M 41/40
See application file for complete search history.

(56) References Cited

U.S. PATENT DOCUMENTS

| 4,001,090 A | 1/1977 | Kalina |
| 4,169,010 A * | 9/1979 | Marwil ................. C12M 27/22 |
| | | 435/247 |

(Continued)

FOREIGN PATENT DOCUMENTS

| WO | 93/03135 | 2/1993 | |
| WO | WO-9303135 A1 * | 2/1993 | ............ C12M 25/00 |

(Continued)

OTHER PUBLICATIONS

Parkes, John R., Gerard Sellek, Gordon Webster, Derek Martin, Erik Anders, Andrew J. Weightman and Henrik Sass. "Culturable prokaryotic diversity of deep, gas hydrate sediments" Environmental Microbiology (2009) 11(12), 3140-3153. (Year: 2009).*

(Continued)

*Primary Examiner* — Michael L Hobbs
(74) *Attorney, Agent, or Firm* — Stein IP, LLC

(57) ABSTRACT

The present invention relates generally to an integrated system, apparatus and method that allows for the continuous culturing of microorganisms under high pressure conditions and at a wide range of temperatures. More specifically, the system is configured to be gas tight and operate under aerobic or anaerobic conditions. The system is also configured to permit periodic sampling of the incubated organisms under such conditions with minimal physical/chemical disturbance inside the reactor and minimal impacts of shear forces on the collected biomass.

16 Claims, 11 Drawing Sheets

(51) Int. Cl.
*C12M 1/00* (2006.01)
*C12M 1/26* (2006.01)

(56) References Cited

U.S. PATENT DOCUMENTS

| | | | |
|---|---|---|---|
| 5,342,580 A | 8/1994 | Brenner | |
| 5,571,720 A | 11/1996 | Grandics et al. | |
| 2002/0172629 A1 | 11/2002 | Jahn et al. | |
| 2007/0042490 A1* | 2/2007 | Welter | C12M 23/24 |
| | | | 435/325 |
| 2009/0126260 A1* | 5/2009 | Aravanis | C07C 4/06 |
| | | | 44/308 |

FOREIGN PATENT DOCUMENTS

| | | | | |
|---|---|---|---|---|
| WO | WO 2012080421 A1 * | 6/2012 | | C07C 1/24 |
| WO | 2013/004670 A1 | 1/2013 | | |

OTHER PUBLICATIONS

Parkes et al., "Culturable prokaryotic diversity of deep, gas hydrate sediments: first use of a continuous high-pressure, anaerobic, enrichment and isolation system for subseafloor sediments (DeepisoBUG)", Environmental Microbiology, 11(12):3140-3153 (2009).

Nomura et al., "Pressure-Regulated Fermentation: A Revolutionary Approach That Utilizes Hydrostatic Pressure", Reviews in Agricultural Science, 2:1-10 (2014).

"Needle Valves Options", Parker Autoclave Engineers, pp. 1-4 (2013).

International Search Report issued in corresponding International Application No. PCT/US2015/018004 dated Jun. 1, 2015.

* cited by examiner

HIGH PRESSURE BIOREACTOR

STATEMENT OF INTEREST

This invention was made with Government support under NSF-OCE Grant Nos. 1038114, 0752221, 1136608, and 1155246. The U.S. Government has certain rights in the invention.

FIELD OF THE INVENTION

The present invention relates generally to an integrated system, apparatus and method that allows for the continuous culturing of microorganisms under high pressure and a wide range of temperature conditions. More specifically, the system is configured to be gas-tight and allow for the employment of media enriched in dissolved gases, under aerobic or anaerobic conditions. The system is also configured to permit periodic sampling of the incubated organisms under such conditions with minimal physical/chemical disturbance inside the reactor.

BACKGROUND OF THE INVENTION

Microbial culturing experiments at high pressures have implications in food science, virus-related research and studies involved in the development of energy resources. Because oxygen solubility is increased at high pressure, the occurrence of large dissolved oxygen tension induces biological oxidative stresses that can affect the function of biological membranes, the physical/-chemical properties of enzymes and regulate virulence and toxin production in pathogens (Follonier et al., Pressure to kill or pressure to boost: a review on the various effects and applications of hydrostatic pressure in bacterial biotechnology, Appl. Microbiol. Biotechnol., 93: 1805-1815, 2012, and references cited therein). Therefore, the food industry has been developing protocols to inactivate microorganisms by applying pressure stresses without the use of temperature treatment that alters food properties (Id.). That pathogens become inactive under high hydrostatic pressure while maintaining intact the interactions and structures required to induce immune responses also makes high pressure microbial studies relevant for the development of high-pressure vaccines (Id.). Future studies on the antibiotic resistance of gram-negative bacteria may be linked to high pressure incubations of extremophile organisms similar to those thriving in the deep ocean (e.g. Alain et al., *Marinitoga piezophila* sp. nov., a rod-shaped, thermo-piezophilic bacterium isolated under high hydrostatic pressure from a deep-sea hydrothermal vent., Int. J. Syst. Evol. Microbiol. 52: 1331-1339 (2002); Takai et al., *Thiomicrospira thermophilia* sp. nov., a novel microaerobic, thermotolerant, sulfur-oxidizing chemolithomixotroph isolated from a deep-sea hydrothermal fumarole in the TOTO caldera, Mariana Arc, Western Pacific. Int. J. Syst. Evol. Microbiol. 54: 2325-2333 (2004)). High pressure microbial studies are also focused on the development of high-pressure vaccines.

High pressure continuous culturing approaches can also affect our understanding of microbial processes associated with petroleum biodegradation and evolution deep in the Earth's subsurface. Recent studies have reported the microbial formation of diesel-like hydrocarbons by *Escherichia coli* strains (Choi et al., Microbial production of short-chain alkanes, Nature, 502, 571-574, 2013). Native microbial populations in petroleum reservoirs include a wide range of anaerobic bacteria and archaea that are commonly found in deep-sea hydrothermal vents (e.g. Head et al., biological activity in the deep subsurface and the origin of heavy oil, Nature, 426, 344-352. (2003). *Thermococcus, Archaeoglobus,* and *Thermotoga*) (Head et al. 2003). Bacteria capable of petroleum biodegradation or synthesis at in-situ high pressure and temperature, however, have not been isolated yet. Moreover, there are many other challenges in the area of high pressure microorganisms that could be overcome with development of the proper culturing and sampling systems. One such challenge may be overcome by the future integration of sampling petroleum systems with laboratory incubations at in-situ pressures.

For at least the above reasons, there is a need to provide systems and methods to study the rates of microbially-mediated petroleum degradation and the efficiency of aerobic microorganisms for biofuel synthesis at pressure and temperature conditions resembling those of the Earth's interior. More broadly, there is a need to provide systems and methods to study different types of microorganisms under high pressure and, in some circumstances, high temperature conditions while permitting periodic, non-damaging sampling of the incubated organisms.

SUMMARY

Broadly stated, the present invention provides an integrated system, apparatus and method that allows for the continuous culturing of microorganisms under high pressure and, optionally, high temperature conditions. The system is designed to operate under gas-tight conditions and allow for the employment of media enriched in dissolved gases, aerobically or anaerobically.

More specifically, the invention embraces a method to allow for the continuous culturing of microorganisms under high pressure, the method comprising: providing a bioreactor capable of withstanding pressures of up to about 150 MPa; pre-enriching media solution with dissolved gases in a reservoir; filling the bioreactor with growth media at high pressure and at the optimal temperature for growth; inoculating the bioreactor with culture; operating the bioreactor under batch mode while the microbial community grows in density to a desired value; operating the bioreactor in the continuous mode by adding a continuous flow of media; increasing the pressure up to at least 40 MPa; and monitoring the growth by sampling the reactor without affecting the hydrostatic pressure (less than 1% pressure fluctuation at 50 MPa) of the microbial community inside the bioreactor.

In an embodiment of the invention the pressure in the bioreactor is about 150 MPa.

In an embodiment of the invention, the reactor is sampled using at least three valves arranged in series. This configuration helps prevent cell lysis of the cultured bacteria. In one embodiment the valves are on/off micrometering valves.

In one embodiment of the invention, the system and method permit periodic sampling of the incubated organisms under such conditions with minimal physical/chemical disturbance inside the reactor.

Another embodiment of the invention provides for a high pressure bioreactor for the continuous culturing of microorganisms under high pressure, the bioreactor comprising: a reactor vessel capable of operating under a pressure up to about 150 MPa; a pressure regulator to measure and regulate the pressure of the reactor vessel; and a sampler that will not affect the hydrostatic pressure of the microbial community in the bioreactor while the reactor contents are sampled.

The bioreactor may operate under aerobic or anaerobic conditions. Moreover, the bioreactor may function as a chemostat, retentostat or batch reactor.

In another embodiment of the invention, the bioreactor further includes an agitator to homogenize the contents of the reactor vessel.

It is to be understood that both the foregoing general description and the following detailed description are exemplary and explanatory and are intended to provide further explanation of the invention as claimed.

DESCRIPTION OF THE DRAWINGS

The invention is more fully described by reference to the accompanying drawings wherein.

DETAILED DISCUSSION

The integrated system and method of the claimed invention allows for the culturing of microorganisms under high hydrostatic pressures (e.g., greater than about 50 MPa, 100 MPa or 150 MPa) across a wide range of temperatures (e.g., 25-500° C.). For example, in one embodiment of the invention, the bioreactor operates at a pressure of about 150 MPa and a temperature of about 25° C. In another embodiment of the invention, the bioreactor operates at a pressure of about 50 MPa and a temperature of about 500° C.

The system may be operated, for example, as i) a chemostat providing continuous flow of gas-enriched media, ii) a retentostat by restricting the outflow of microorganisms from the reaction cell, or iii) a batch reactor whereby media delivery is stopped and the reactor is sealed to allow for microbial growth under a confined chemical environment. Closed system batch experiments evaluate the full cycle of microbial metabolism from initial growth to cell death, while a continuous culture flow-through approach allows for the assessment of specific relations between different metabolic pathways and microbial adaptability across a spectrum of constant anaerobic and aerobic conditions.

Figure 1:
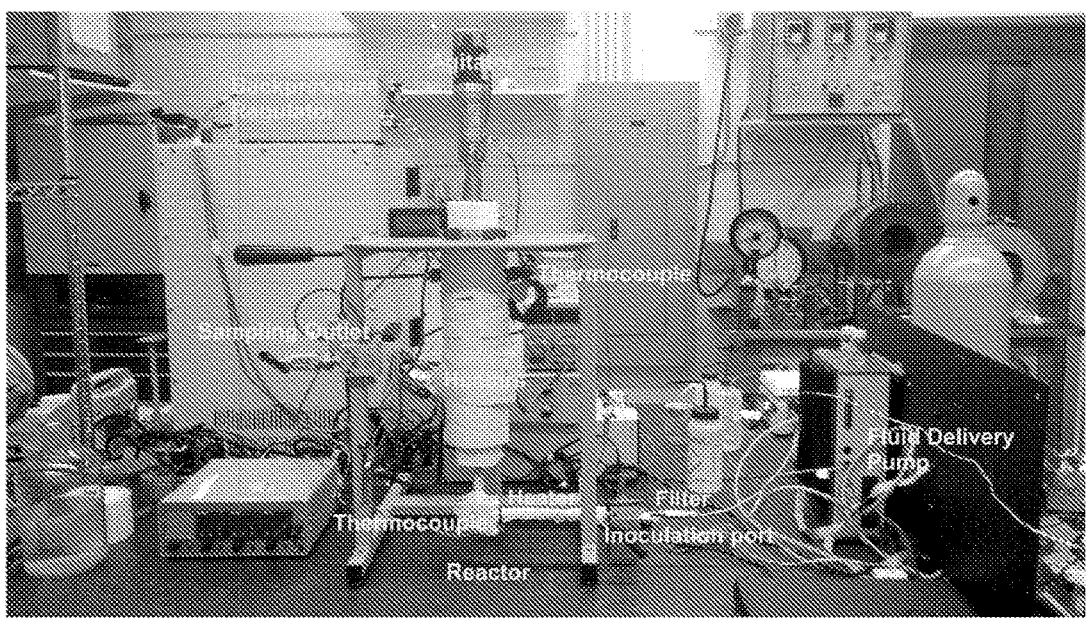
FIG. 1 is a photograph of an embodiment of the high pressure bioreactor.
Figure 6:
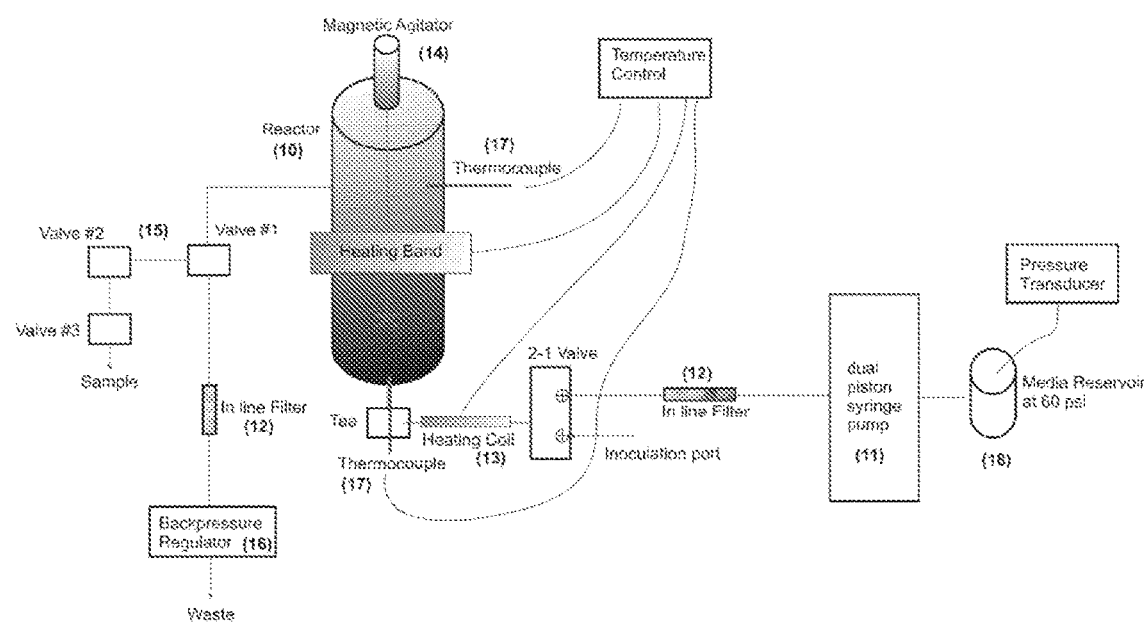
FIG. 6 is a schematic drawing of the high pressure bioreactor.

FIG. 1 provides a photograph of a high pressure bioreactor of the claimed invention. FIG. 6 provides a schematic drawing of the high pressure bioreactor (10). In this embodiment, fluid delivery is provided by a syringe pump (11). Media is transported by the pump to the reactor. In line filters (12) are used to reduce the risk of contamination. Media is preheated (13) prior to introduction in the reaction cell. Here, media and cultures are homogenized at high pressure with the use of a magnetic agitator (14). A sampling scheme (15) composed of three on/off and micrometering valves permits high pressure sampling with minimal impacts of shear forces developed during decompression to ambient conditions. Elevated pressure conditions (e.g., greater than 50 MPa) are maintained constant with a digital backpressure regulator (16). The initial inoculation of the reactor is conducted through one of the inlets of the system. Titanium sheathed thermocouples (17) are placed in contact with the media inside the reactor.

Figure 2:
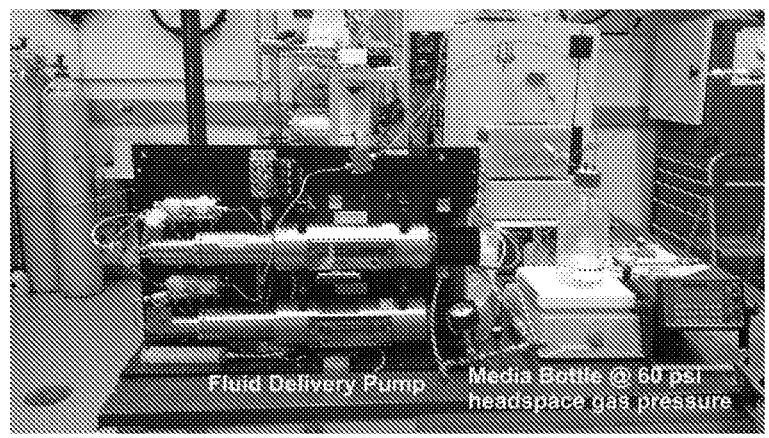
FIG. 2 is a photograph of an embodiment of the high pressure bioreactor, focusing on the media bottle. Media enriched in dissolved gases (e.g. $H_2$, $CO_2$, $N_2$, $O_2$) is delivered by the gas-tight high-pressure syringe pump.
Figure 3:
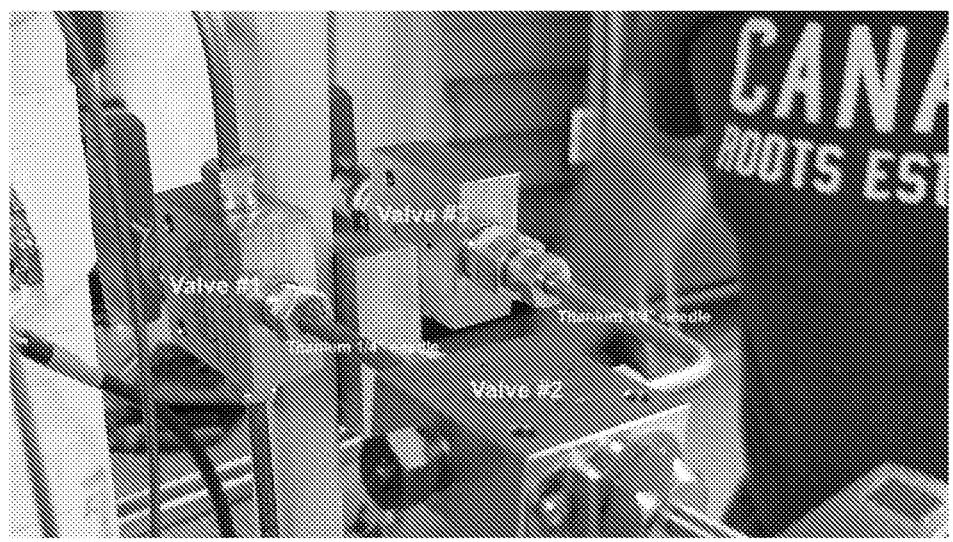
FIG. 3 is a photograph of the valve arrangement employed to subsample without affecting the hydrostatic pressure of the microbial community in the bioreactor and without subjecting the collected biomass to high shear forces.

As shown in FIGS. 1 and 6, the main component of the high pressure bioreactor system is a fixed volume (115 ml) cylindrical reactor that allows microbial communities and media to be homogeneously mixed at high hydrostatic pressures and temperatures. Media is delivered in a continuous and pulse-free fluid flow by a high precision syringe pump under gas-tight conditions. Media solution is pre-enriched with dissolved gases (e.g. $H_2$, $N_2$, and $O_2$) at user-determined concentrations in a reservoir bottle (18) that can withstand 60 psi of headspace partial pressure, measured by a high precision digital pressure transducer (see FIGS. 2 and 6). Upon opening a series of valves between the gas-charged fluid reservoir, the syringe pump and the bioreactor, media flow takes place at precisely controlled rates. By adjusting flow rates of fluid delivery, the residence time of the reactant fluids in the bioreactor may be controlled, thus constraining the growth rate of microorganisms. Each heating zone is independently controlled and in-situ monitored by temperature controllers with auto-tuning capabilities to provide maximum thermal stability. Media solutions are pre-heated prior to entering the reaction cell, minimizing thermal perturbations developed during fluid mixing in the bioreactor. The system is designed to provide a precise and fine adjustment of the temperature conditions while minimizing thermal gradient, thus allowing for the culturing of microorganisms at their optimal temperature of growth. Constant pressure conditions are maintained under continuous media flow with a backpressure regulator.

Other unique and novel aspects of the high pressure bioreactor design include i) the direct inoculation of the bioreactor and ii) subsampling under high hydrostatic pressure. At the initial stage of the experiment, the bioreactor is filled with growth media at atmospheric pressure and at the optimal temperature for growth. Direct inoculation is commenced through one of the five inlets/outlets by injecting 2.5 ml of pre-inoculum. The bioreactor remains under batch mode while the microbial community grows in density to the desired values. Then, continuous flow starts at rates ranging from 18 nL/min to 15 mL/min. For example, flow rates of 0.020 mL/min yield residence times of nearly 4 days.

Figure 4:
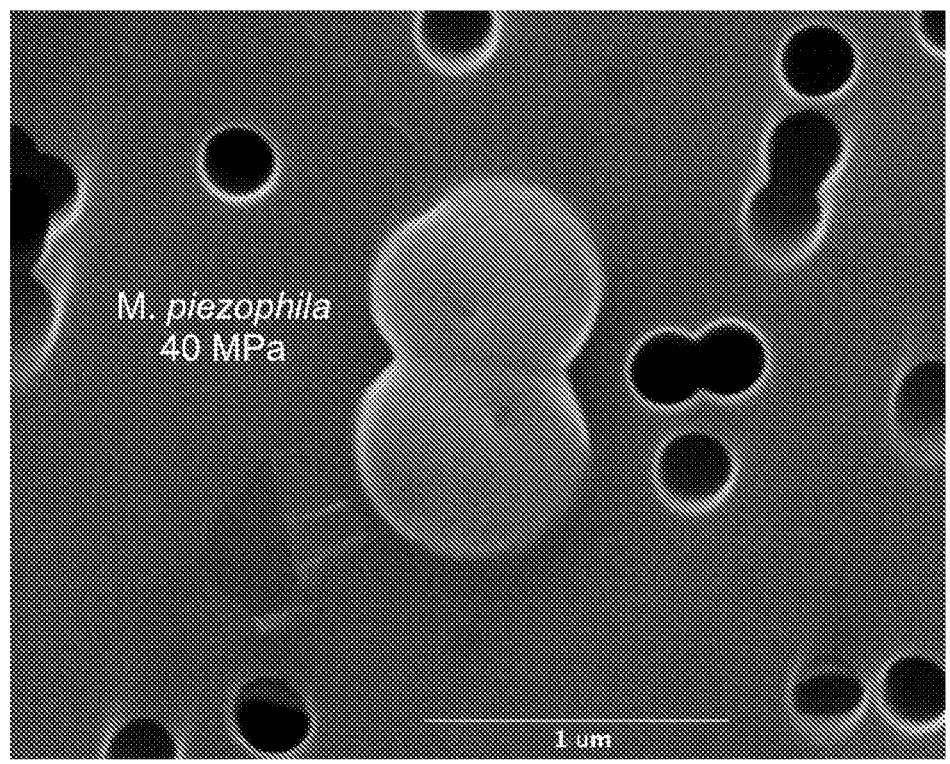
FIG. 4 is a scanning electron microscope image depicting intact cells sampled at 40 MPa.

Subsampling Technique:

A series of micrometering valves ensure the retrieval of subsamples without affecting the hydrostatic pressure of the microbial community in the bioreactor and without subjecting the collected biomass to high shear forces (FIG. 4). Sampling commences by sequentially opening the valves #1, #2, and the micrometering valve #3. The deadspace inside the valves and connecting titanium ¼" OD tubing (i.e., needles) is prefilled with deionized water to eliminate depressurization when valves #1 and #2 are opened. The first 4 mL of aliquot collected are discarded. The rate of sampling is controlled by the position of the micrometering valve #3, while maintaining constant pressure inside the bioreactor (less than 1% pressure fluctuation at 50 MPa). During sampling, the valves #1 and #2 are fully open and the magnetic agitator is turned off. Samples for microbiological and molecular analysis are retrieved by closing the valve #1 and by fully opening the micrometering valve #3. The cells presented in the fluid media trapped inside the deadspace of the sampling arrangement (FIG. 4) represent the intact microbial population cultured in the bioreactor. The subsampling scheme eliminates cell lysis effects imposed by decompression of the sampled organisms to atmospheric pressure and by fluid flow path through the microscopic orifice of the final micrometering valve. Cells collected in our pilot experiments appear intact and show cell division morphology (4, 8). Sampled cells have also been documented to be labile in post-sampling transfer to hungate culture tubes at atmospheric pressure.

The inventor conducted a series of experiments under high hydrostatic pressure conditions. Subsamples were collected on regular time steps. These experiments illustrate the efficiency and the user-friendly nature of the integrated culturing system.

EXAMPLES

High Pressure Continuous Culturing of Extremophiles

Example 1

*Thiomicrospira Thermophile* (Aerobic, Mesophilic, Autotrophic)

In this set of experiments, the inventor cultured the sulfur oxidizing extremophile bacteria *Thiomicrospira thermophila* (gram negative) which has been isolated from hydrothermal vents at East Pacific Rise, at 2500 meter depth, and has been shown to have grown with thiosulfate as the electron donor under aerobic and optimal temperature of 35° C. (60 min doubling time) (Takai et al., *Thiomicrospira thermophila* sp. nov., a novel microaerobic, thermotolerant, sulfur-oxidizing chemolithomixotroph isolated from a deep-sea hydrothermal fumarole in the TOTO caldera, Mariana Arc, Western Pacific, IJSEM, 2004). Here, the inventor incubated *T. thermophila* at high hydrostatic pressures and by utilizing an autotrophic media solution enriched with $O_{2(g)}$. The unbuffered seawater salinity medium contained the following ($L^{-1}$): 25 g NaCl, 0.2 g $NH_4Cl$, 1.23 g $MgCl.6H_2O$, 0.4 g $CaCl_2.2H_2O$. After autoclaving, the following filter-sterilized solutions were added (by volume): 10% $K_2HPO_4$ (0.25 g in 500 mL), 10 wt % $NaHCO_3$ (2.52 g in 500 mL), 1 wt % trace metal solution SL-10, and ~6 wt % $Na_2S_2O_3.5H_2O$ (16 g in 500 mL). The trace metal solution SL-10 is made as follows (in 1L): 1.5 g $FeCl_2.4H_2O$ dissolved in 10 mL 25 wt % HCl, 70 mg $ZnCl_2$, 100 mg $MnCl_2.4H_2O$, 6 mg $H_3BO_3$, 190 mg $CoCl_2.6H_2O$, 2 mg $CuCl_2.2H_2O$, 24 mg $NiCl_2.6H_2O$, 36 mg $Na_2MoO_4.2H_2O$. The inventor evaluated the effect of pressure on the rates of metabolic growth and formation of metabolic byproducts (elemental sulfur, sulfate).

Experiments were conducted in the bioreactor at 0.1, 5 and 10 MPa (1450 psi), at 35° C. The organism metabolizes through sulfur transformation reactions involving formation and subsequent oxidation of elemental sulfur (Houghton et al, Biogeochemistry of seafloor hydrothermal vent systems: an experimental study conducted at in situ conditions, PhD Thesis, 170 pp, University of Minnesota, Minn., 2013; Takai et al. 2004). The transformation of sulfur was carried on by two distinct reaction pathways that lead to the formation of elemental sulfur and $SO_4^{2-}$:

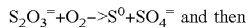

$S_2O_3^= + O_2 \rightarrow S^0 + SO_4^=$ and then

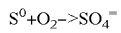

$S^0 + O_2 \rightarrow SO_4^=$

Precipitation of elemental sulfur did not compromise the performance of the experimental system.

Figure 5A:
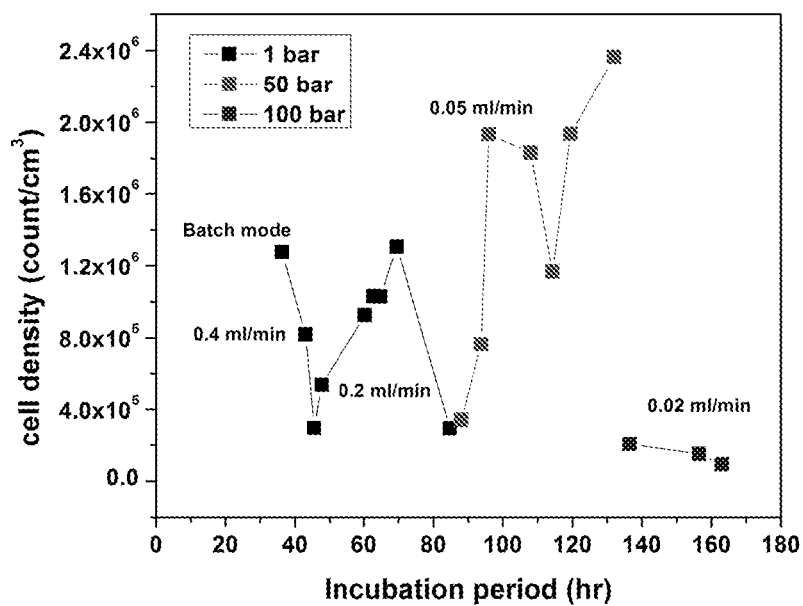
FIGS. 5a and 5b provide plots of cell density (FIG. 5a) and $SO_4^{2-}$ (FIG. 5b) in a time series of subsamples of *T. microspira* continuous culturing under high hydrostatic pressure conditions.
Figure 5B:
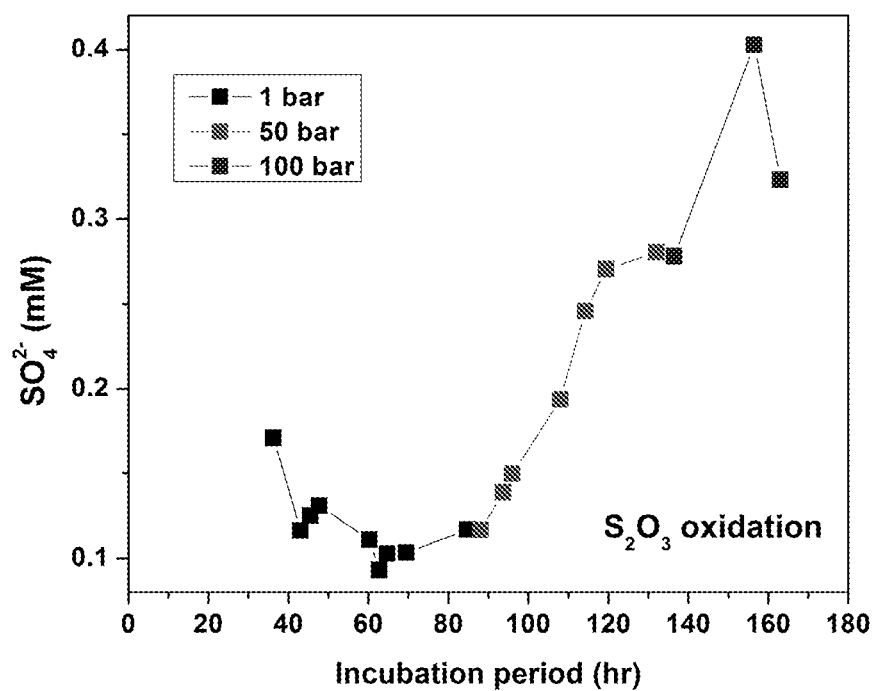

During the course of the experiment, the inventor studied the growth and metabolic efficiency of *T. microspira* as function of the flow rate and pressure (FIGS. 5a and 5b). After direct inoculation of the chemostat, the community was not disturbed and allowed to increase cell density under batch mode operation (0-37 hr). Continuous culturing was initiated at 0.4 mL/min, at 0.1 MPa (14.5 psi), while monitoring both the cell density and the concentrations of the metabolic byproduct $SO_4^{2-}$. After 85 hours of incubation, the pressure was increased to 5 MPa (~750 psi) and the media flow rate was adjusted to 0.05 mL/min (FIGS. 5a and 5b). At these conditions, the microbial community appears to establish a steady state population, after a short period of exponential growth (~20 hr). The concentrations of dissolved $SO_4^{2-}$ also increased to nearly 0.3 mM, reflecting the efficiency of microbially mediated thiosulfate oxidation at 5 MPa. After 132 hr of total incubation, fluid flow rate was decreased to 0.02 mL/min and pressure was increased to 10 MPa. Cell counts reveal that such high hydrostatic pressure conditions induced stress on the microorganisms and suppressed growth (FIG. 5a). However, growth was evident in all the subsamples documented by the presence of dividing cells in the microscope images. Furthermore, the concentrations of dissolved $SO_4$ in the high-pressure inoculum were increased to 0.4 mM. The subsampled inocula also grew in post-growth bottles on the bench, although at slower rates than expected, indicating that cells were labile even though growth was suppressed under pressure-induced stress.

Example 2

Continuous Culture of *M. Piezophila* Under High Pressure and Varying Dilution Rates The inventor conducted a series of pilot experiments, continuously culturing aerobic/mesophilic and anaerobic/thermophilic bacteria under high hydrostatic pressure conditions. These were nearly 2-week long experiments in which, after the initial inoculation of the bioreactor, the only variables manipulated were pressure and the fluid flow rate. Subsamples were collected on regular time steps. These experiments illustrate the efficiency and the user-friendly nature of the integrated culturing system.

Pilot experiments evaluating the effect of pressure on the fermentative growth of *M. piezophila* at an optimal temperature of growth of 65° C. (Alain et al., *Marinitoga piezophila* sp nov., a rod-shaped, thermo-piezophilic bacterium isolated under high hydrostatic pressure from a deep-sea hydrothermal vent, *International Journal of Systematic and Evolutionary Microbiology*, 52, 1331-1339, 2002) were designed to demonstrate the capabilities of the high-pressure bioreactor. At the initial stage of the experiment, the bioreactor was filled with growth medium solution at ambient pressure and heated at 65° C. Direct inoculation was commenced through the 2-1 pressure valve by injecting a 2.5 ml of pre-inoculum in the 115 ml of media in the bioreactor (FIG. 6). The system remained under batch mode at atmospheric pressure for ~30 hours while the microbial community grew in density from $1.2 \times 10^6$ to $2 \times 10^6$ cells/ml (Table 1), in accordance with initial continuous culture protocols described by Harder et al (Microbial selection in continuous culture, *J Appl Bacteriol*, 43(1), 1-24, 1977). Continuous medium flow was established for the reminder of the experiment, with flow rates decreasing from 2 ml/min to 0.16 ml/min and to 0.025 ml/min, each corresponding to media residence times inside the reactor of 1 to 12 to 77 hours.

The pressure manipulations imposed during this trial were performed in the following order (time interval): 0.1 MPa (24 h); 10 MPa (31.5 h); 20 MPa (38 h); 30 MPa (51 h); 40 MPa (90 h), 30 MPa (19 h); 20 MPa (23 h); 10 MPa (22.5 h) and 0.1 MPa (17.5 h). The estimated specific growth rates ($\mu$) under continuous medium flow were constrained by both pressure and dilution rate. Dilution rate (D), defined as the ratio between flow rate and the volume of the bioreactor (Herbert et al., The continuous culture of bacteria; a theoretical and experimental study, *J Gen Microbiol*, 14(3), 601-622, 1956; Fencl, Theoretical analysis of continuous culture systems, in *Theoretical and Methodological Basis of Continuous Culture of Microorganisms*, edited by Malek I. and Fencl Z., pp. 69-235, Academic Press, New York, 1966), ranged from 1.043 to 0.013 h$^{-1}$ (Table 1). The magnetic agitator operated at 70-100 rpm through the course of the experiment. Continuous culture of *M. piezophila* was conducted unremittingly for 352 hours (Table 1).

Figures 7A, 7B:
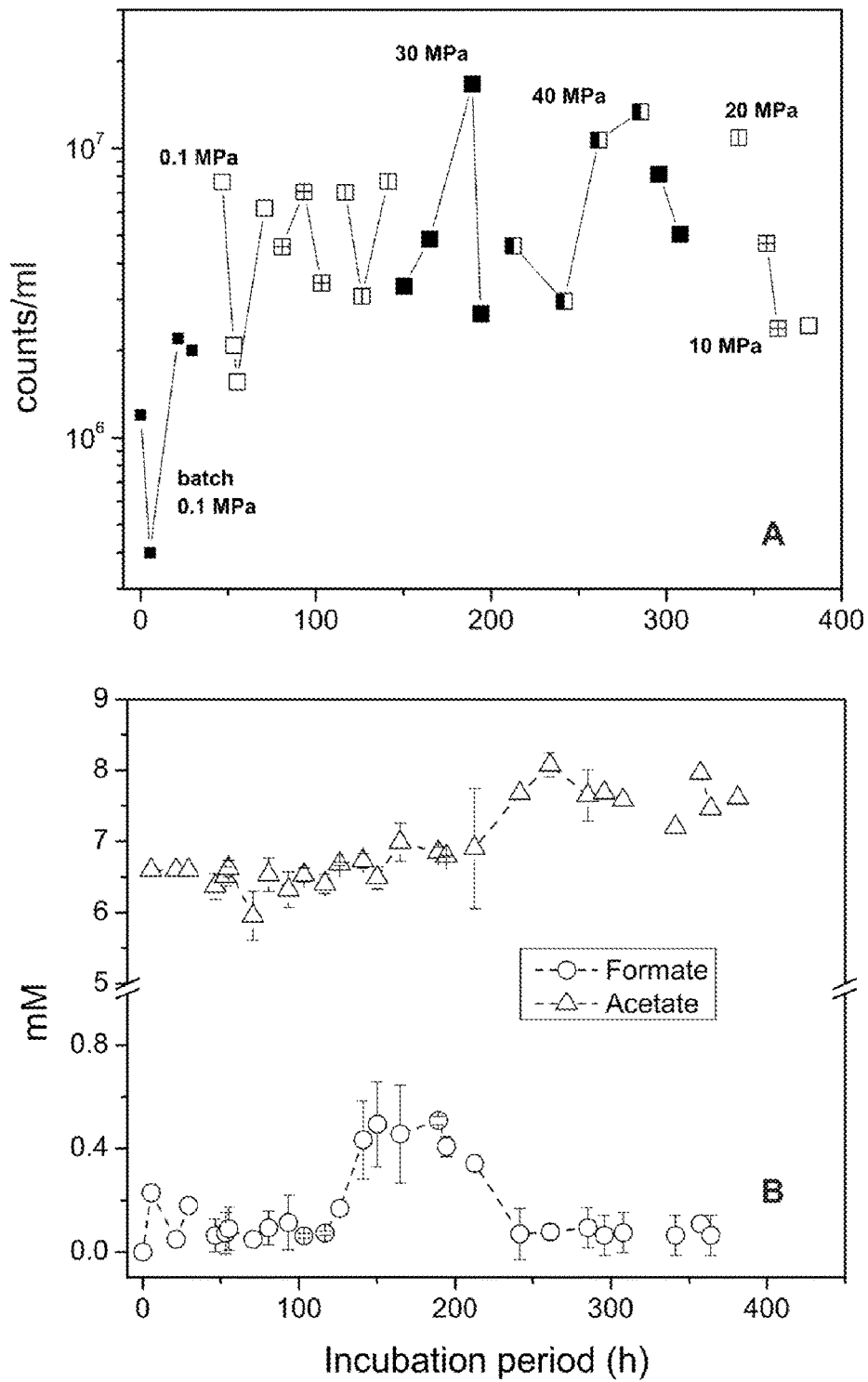
FIGS. 7a and 7b provide plots of cell density (FIG. 7a) and formate/acetate concentration (FIG. 6b) in a time series of subsamples of *M. piezophila* under high hydrostatic pressure conditions.

Initial continuous culturing was performed at 2 ml/min under 0.1 MPa for 8.5 hours, with a transition to 0.16 ml/min for the last 15.5 hours before changing to 10 MPa. At this pressure, media flow remained at 0.16 ml/min and incubations lasted for 31.5 hours (FIG. 7a). A second increase in pressure (20 MPa) was performed for the next 40 hours with a third and final adjustment in medium flow rate of 0.025 mL/min for the last 15 hours of incubations in this set. The remainder of the run maintained at 0.025 mL/min with pressures increasing up to 40MPa. The final sub-set of incubations were performed by gradually decreasing pressure from 40 MPa to 30 (for 19 h), 20 (for 23 h), 10 (for 22.5 h) and 0.1 MPa (for 17.5 h) at constant flow rate of 0.025 ml/min (Table 1, FIGS. 7a and 7b).

Figure 8:
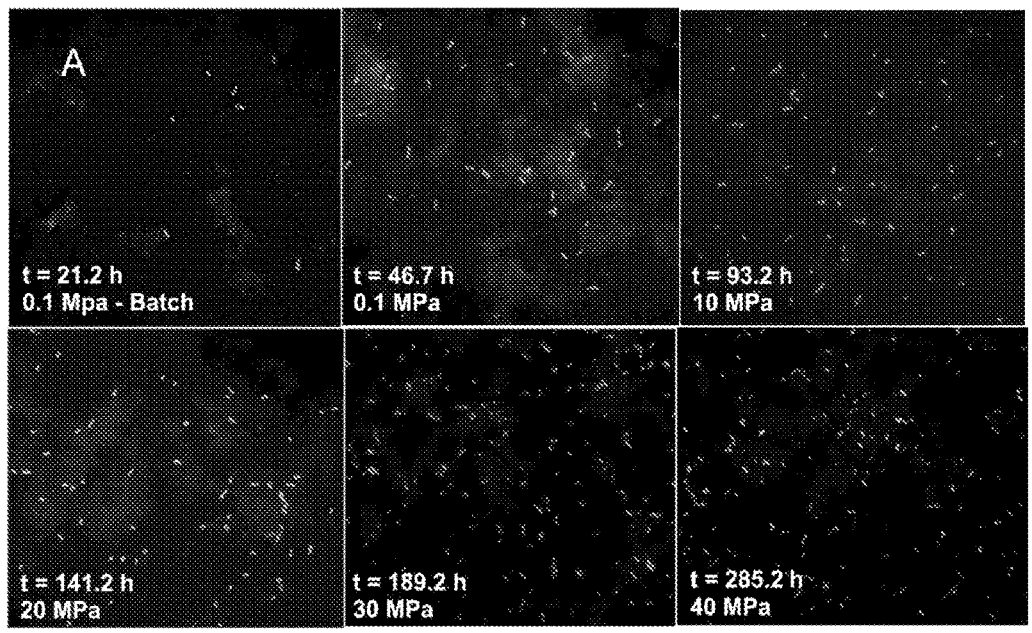
FIG. 8 provides the morphology and density of *M. piezophila* growing at high hydrostatic pressure conditions.

Overall, growth was evident in all the stages of the experiment documented by increases in cell numbers during direct cell counts under fluorescent microscopy (FIGS. 4 and 8). Cells collected in our experiments appeared intact and were actively dividing (FIGS. 4 and 8). Sampled cells were also shown to be viable in post-sampling transfers to hungate culture tubes at atmospheric pressure. Initial dilution rates of 1.043 h$^{-1}$ at 0.1 MPa suppressed the accumulation of microbial biomass after the initial cell density enrichment produced during batch mode. In order to avoid complete wash-out of cells, the dilution rate was decreased to 0.083 h$^{-1}$ (flow rate 0.16 ml/min) resulting in a cell count increase (0.1 MPa). At pressures between 0.1-20 MPa and flow rate of 0.16 ml/min, the density of the population maintained relatively constant with values ranging between $3.42 \times 10^6$ and $7.04 \times 10^6$ cells/ml, with an average of $5.23 \times 10^6 \pm 1.81 \times 10^6$ cells/ml (Table 1) (FIG. 7a). At the higher pressures of 30 and 40 MPa (flow rate 0.025 ml/min; D=0.013 h$^{-1}$), cell counts reached values of $1.67 \times 10^7$ and $1.34 \times 10^7$ cells/ml with $\mu$ values of 0.042 and 0.034 h$^{-1}$, respectively (Table 2). This increase in cell density is indicative of the piezophilic nature of the microorganism, as previously reported ($P_{opt}$=40 MPa) by Alain and others (2002).

Figure 9:
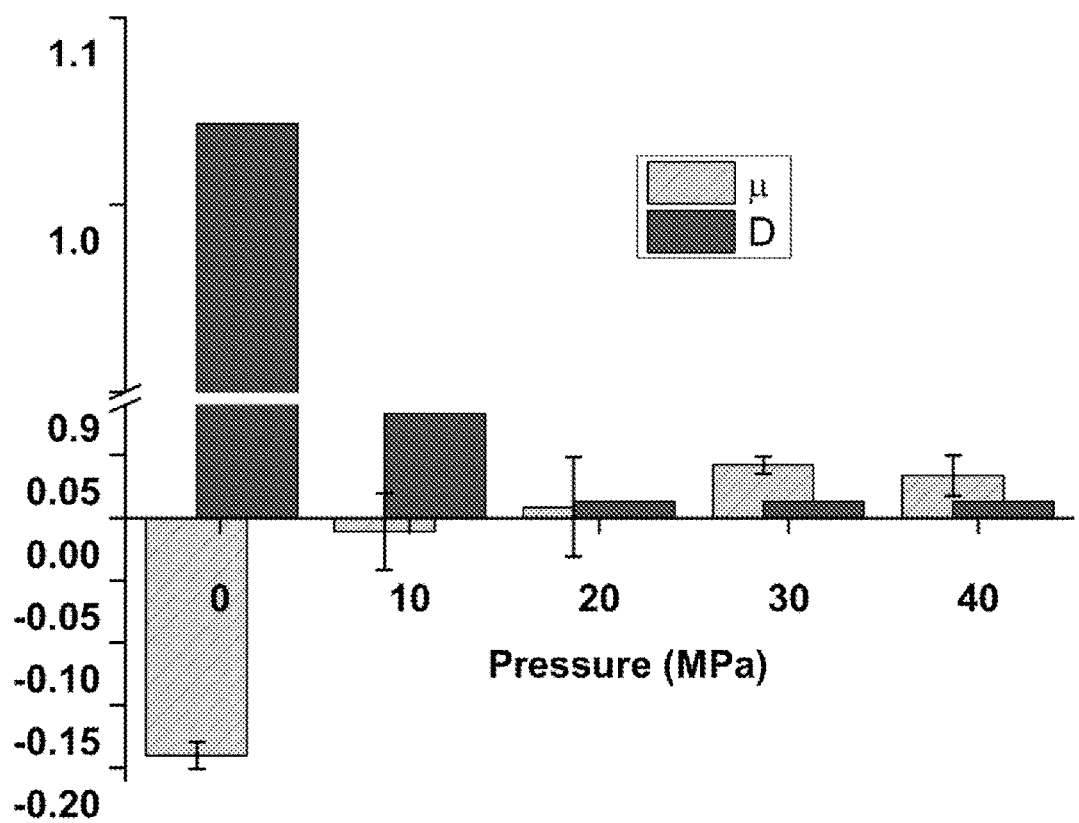
FIG. 9 provides a graph showing the specific growth rate ($\mu$) and dilution rate (D) as a function of pressure for *M. piezophila* growing at high hydrostatic pressure conditions.

The relationship between dilution rate and specific growth rate dictates the sustainability of the microbial population during continuous culture (Herbert et al., 1956; Fencl, 1966). For conditions corresponding to D>$\mu$, like those exemplified, at 0.1 (47-55 h) and 10 MPa (81-103 h), instances of wash-out conditions suppressed biomass accumulation (FIG. 9). At 20 MPa (117-141 h), D=$\mu$ and the population appears to be in a steady state. Exponential growth was observed at 30 (150-189 h) and 40 MPa (242-285 h) when D<$\mu$. However, the piezophilic nature of *M. piezophila* combined with low D conditions shifted growth from exponential to death phase. Under these conditions, which mimic batch culture, decline in growth could be induced by depletion of the limiting substrate concentration inside the bioreactor. Regardless, the inventors are able to document the self-adjusting activity of *M. piezophila* through increasing and decreasing population densities (either through wash-out or restricted growth due to substrate limitation) in order to maintain a general steady state.

*M. Piezophila* Fermentation Metabolism

During the course of the experiment, dissolved formate was also monitored as metabolic byproduct of mixed acid fermentation to help inform the extent of *M. piezophila* fermentative growth. The concentrations of formate produced appear to follow cell concentrations, with maximum values of 0.51±0.02 mM observed at 30 MPa. At this point, the highest specific growth rates of 0.042±0.007 h$^{-1}$ were attained (FIG. 7b, Table 1, 2). The initial concentration of the dissolved acetate in the medium was ~6 mM. Following *M. piezophila* growth with pressure increase, acetate was accumulated in the bioreactor as a byproduct of fermentation as well. The highest concentration of ~8 mM was reached at 40 MPa and maintained throughout the course of the experiment, further supporting the minimal contribution of acetate as carbon source to the growth of *M. piezophila* (Alain et al., 2002). Similar acetate utilization effects have also been observed in *M. okinawensis* (Nunoura et al., *Marinitoga okinawensis* sp nov., a novel thermophilic and anaerobic heterotroph isolated from a deep-sea hydrothermal field, Southern Okinawa Trough, *International Journal of Systematic and Evolutionary Microbiology*, 57, 467-471, 2007). The specific growth rates attained at all pressures were significantly smaller than those determined by Alain et al. (2002) (Table 2), reflecting the important contribution of elemental sulfur respiration on the heterotrophic growth of the microorganism in comparison to fermentation. Similar to our observations, Alain et al. (2002) reports slow growth of *M. piezophila* during fermentation in the absence of elemental sulfur.

Description of *M. Piezophila* Continuous Growth

Throughout the continuous culture of *M. piezophila*, microbial growth was adjusting to the different pressures and dilution rates. Considering the relationship between dilution rate and substrate availability on microbial growth during continuous culture, the growth patterns of *M. piezophila* at different pressures can be described following the Monod equation (Monod, *Recherches sur la croissance des Cultures Bactériennes*, Hermann, Paris, 1942, Monod, The growth of bacterial cultures, *Annual Review of Microbiology*, 3, 371-394, 1949; Herbert et al., 1956; Fencl, 1966; Harder et al., 1977):

$$\mu = \mu_{max} \frac{s}{K_s + s} \quad \text{(eq. 1)}$$

where s is the concentration of the limiting growth substrate measured at the outflow of the bioreactor and $K_s$ is the substrate concentration at which $\mu = \mu_{max}/2$. The $\mu_{max}$ can be assumed that approximates the maximum specific growth rate measured in batch mode experiments (Herbert et al., 1956). While chemostats are considered self-adjusting systems that can reach steady-state conditions at different dilution rates (Harder et al., 1977), complete wash-out occurs when D is greater than a critical value ($D_c$). At this point, the concentrations of s are equal to the concentrations ($S_R$) introduced by the inflowing medium and the $D_c$ is estimated as follows:

$$D_c = \mu_{max} \frac{s_R}{K_s + s_R} \quad \text{(eq. 2)}$$

This is an important parameter as it defines the conditions under which negative growth rates prevail (Herbert et al., 1956; Russell and Cook, Energetics of bacterial-growth—balance of anabolic and catabolic reactions, *Microbiol Rev*, 59(1), 48-62, 1995). Such conditions might have occurred during the growth of *M. piezophila* at 10 MPa (81-103 h) (Table 1, 2), where an instance of negative µ, different from the imposed dilution rate, is documented (FIG. 9). Thus, at points like this one, the culture's decrease in cell densities represents a wash-out stage. Here, assuming that $K_s \ll s_R$ (Herbert et al., 1956) and that yeast extract was the limiting energy carbon source with $s_R = 2$ g/L, then $D_c \sim \mu_{max} \sim 0.083$ $h^{-1}$, corresponding to a doubling time of 8.3 hours. This value is even greater than the specific growth rates attained at 30 and 40 MPa (0.042 and 0.034 $h^{-1}$, respectively); conditions that are expected to reflect the optimum pressure of growth (Alain et al., 2002). However, at these high pressures, µ are positive with values exceeding those of the dilution rates (FIG. 9), and thus, $\mu_{max}$ are expected to be greater than the attained growth rates.

Discussion of Testing and Test Results

Figure 10:
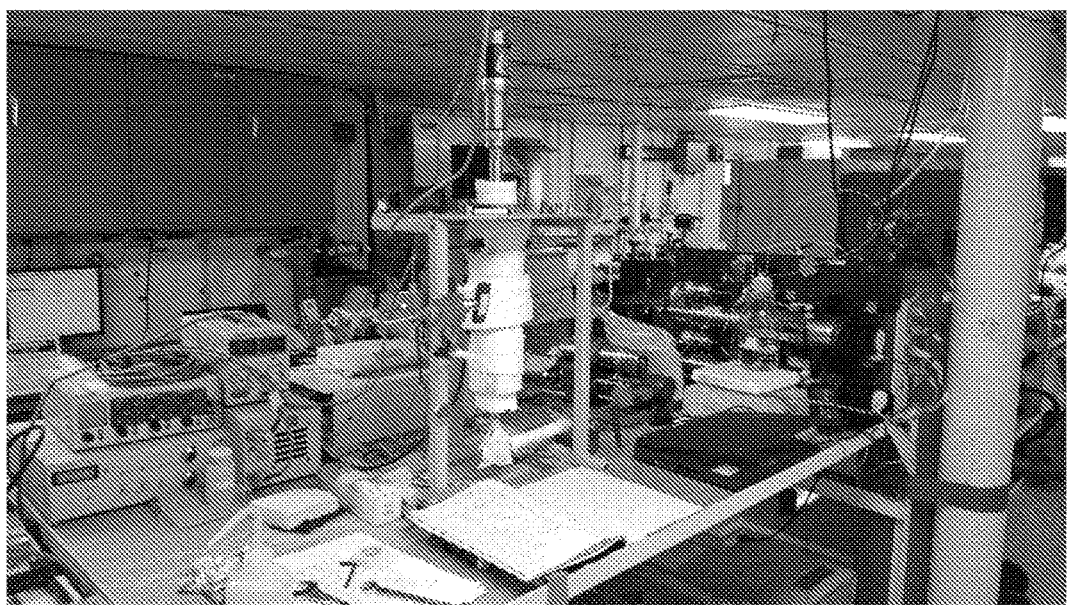
FIG. 10 shows the high-pressure bioreactor deployed onboard the oceanographic vessel R/V Atlantis. Continuous culture experiments of microbial communities collected from deep-sea hydrothermal vents were conducted at in-situ seafloor pressure (25 MPa) and temperature (30-50° C.) conditions without depressurizing the environmental fluid sample by integrating vent fluid sampling techniques (Isobaric-Gas-Tight sampler, WHOI) (Seewald, J. S., et al. (2002), A new gas-tight isobaric sampler for hydrothermal fluids, Deep-Sea Research, Part I: Oceanographic Research Papers, 49(1), 189-196.) with our high pressure bioreactor. Experiments were designed to study denitrification and dissimilatory nitrate reduction to ammonium (DNRA) metabolisms under in-situ deep-sea vent temperature and pressure conditions. The hydrothermal vent sites studied (Crap Spa, Tica) are located along the East Pacific Rise at 9° 51' N and at depth of ~2500 meters.

By documenting the growth of *M. piezophila* under a range of dilution rates and pressures, the inventor has shown the success for continuous time series experiments with non-intrusive sampling. This growth assay demonstrates the effectiveness of the system in maintaining imposed temperature and pressures during a single run, over a period of 382 hours of continuous operation. This setup has also overcome the difficulty of incorporating gaseous substrates such as $H_2$ and $CO_2$ (data not shown; FIG. 10) in high-pressure experiments, and thus, addressing an important experimental barrier for studying many relevant metabolisms under pressure (Takai et al., Cell proliferation at 122° C. and isotopically heavy $CH_4$ production by a hyperthermophilic methanogen under high-pressure cultivation, *Proceedings of the National Academy of Sciences of the United States of America*, 105(31), 10949-10954, 2008). Moreover, contamination was not found to be a real difficulty for the operation of the system, even for nutrient rich media like the one used during *M. piezophila* culturing. These manipulations on medium flow rates and pressure conditions demonstrate that, like dilution rates, microbial activity adjusts to pressure variations to achieve steady state during continuous culture.

The combined temperature/pressure/dilution rate manipulation in the system allows for meaningful spatial and temporal experimentation of microbial processes associated with a broad array of unexplored environmental regimes. For example, this approach will be relevant for addressing the current debate about the size and activity of the deepest biosphere in the subsurface (Whitman et al., Prokaryotes: The unseen majority, *Proceedings of the National Academy of Sciences of the United States of America*, 95(12), 6578-6583, 1998; D'Hondt et al., Distributions of microbial activities in deep subseafloor sediments, *Science*, 306, 2216-2221, 2004; Lipp et al., Significant contribution of Archaea to extant biomass in marine subsurface sediments, *Nature*, 454(7207), 991-994, 2008; Fang et al., Deep-sea piezosphere and piezophiles: geomicrobiology and biogeochemistry, *Trends in Microbiology*, 18(9), 413-422, 2010; Hinrichs and Inagaki, Downsizing the deep biosphere, *Science*, 338(6104), 204-205, 2012; Jorgensen, Shrinking majority of the deep biosphere, *Proceedings of the National Academy of Sciences of the United States of America*, 109(40), 15976-15977, 2012; Kallmeyer et al., Global distribution of microbial abundance and biomass in subseafloor sediment, *Proceedings of the National Academy of Sciences of the United States of America*, 109(40), 16213-16216, 2012; Hoehler and Jorgensen, Microbial life under extreme energy limitation, *Nature Reviews in Microbiology*, 11(2), 83-94, 2013). While it's well accepted that microorganisms are able to cope in spite of these extreme conditions (Morono et al., Carbon and nitrogen assimilation in deep subseafloor microbial cells, *Proceedings of the National Academy of Sciences of the United States of America*, 108(45), 18295-18300, 2011; Lomstein et al., Endospore abundance, microbial growth and necromass turnover in deep sub-seafloor sediment, *Nature*, 484(7392), 101-104, 2012; Orsi et al., Gene expression in the deep biosphere, *Nature*, 499(7457), 205-208, 2013), the way they assess energy status to shift from growing to surviving under maintenance energy conditions to being alive in a dormant stage remains unstudied and represents the foundation for such debate.

By adopting dilution rates as low as those employed in our continuous culture experiment (0.013 $h^{-1}$), the relationship between energy limitation and microbial growth can be explored, by restraining growth rates to lower values than those attained in batch high-pressure cultures (Herbert et al., 1956; Russell and Cook, 1995; Hoehler and Jorgensen, 2013). The fundamental questions on the kinetics, bioenergetics and efficiency of microbial metabolisms, which have remained in its infant stage in the piezosphere, can now be exploited in combination with transcriptomics, proteomics and metabolomics (Hoskisson and Hobbs, Continuous culture-making a comeback?, *Microbiology-SGM*, 151, 3153-3159, 2005). This technological advancement, which allows the onsite incubation of microorganism without depressurization (FIG. 10) or under simulated in-situ physical (temperature, pressure) and chemical (energy status) conditions, will help determine the relevance of experimental pressure-based physiological responses to their in-situ growth in nature (Abe, Exploration of the effects of high hydrostatic pressure on microbial growth, physiology and survival: Perspectives from piezophysiology, *Biosci Biotech Bioch*, 71(10), 2347-2357, 2007).

As a final note, the development of the high-pressure bioreactor is also of practical significance for: i) the synthesis of microbial products in industrial biotechnology (Liu et al., 2007), ii) improving biofuel/bioremediation procedures (Aitken et al., 2004; Feng et al., 2007; Jones et al., Crude-oil biodegradation via methanogenesis in subsurface petroleum reservoirs, Nature, 451(7175), 176-180, 2008) and iii) contributing to high-pressure food processing research (Abid et al., Synergistic impact of sonication and high hydrostatic pressure on microbial and enzymatic inactivation of apple juice, *Lwt-Food Sci Technol*, 59(1), 70-76, 2014; Huang et al., Responses of microorganisms to high hydrostatic pressure processing, *Food Control*, 40, 250-259, 2014; Sansone et al., Effects of high pressure treatments on polymeric films for flexible food packaging, *Packag Technol Sci*, 27(9), 739-761, 2014). The recent documentation of microbially-mediated biodegradation processes in subsurface petroleum reservoirs on one hand (Aitken et al., 2004; Feng et al., 2007; Jones et al., 2008), and that of diesel-like fuel biosynthesis on the other (Schirmer et al., Microbial biosynthesis of alkanes, *Science*, 329(5991), 559-562, 2010; Choi and Lee, Microbial production of short-chain alkanes, *Nature*, 502(7472), 571-574, 2013; Harger et al., Expanding the product profile of a microbial alkane biosynthetic pathway, *ACS Synthetic Biology*, 2(1), 59-62, 2013; Howard et al., Synthesis of customized petroleum-replica fuel molecules by targeted modification of free fatty acid pools in *Escherichia coli*, *Proceedings of the National Academy of Sciences of the United States of America*, 110(19), 7636-7641, 2013), make exemplary subjects for high-pressure continuous culture investigations of key microorganisms relevant to bioengineering. In any case, constraining microbial growth experimentally at elevated pressures will promote our fundamental knowledge of life in the piezosphere and the optimization of biomaterial yields or biological reaction rates for industrial applications.

Experimental Procedures
Bacterial Strains and Analytical Methods

*Marinitoga piezophila* strain KA3$^T$ (DSM 14283; Alain et al. (2002)) is a strictly anaerobic, thermophilic ($T_{opt}$=65° C.), and chemo-ogranotrophic sulfur reducing bacterium that has been shown to grow under elevated pressure conditions ($P_{opt}$=40 MPa, doubling time ~20 min). The strain was isolated from deep-sea hydrothermal environments (13° N East Pacific Rise) at a depth of 2630 m (Alain et al., 2002). In this set of experiments, KA3$^T$ grew in a medium modified from Ravot et al. (*Thermotoga elfii* sp. nov., a novel thermophilic bacterium from an African oil-producing well, *Int J Syst Bacteriol*, 45(2), 308-314, 1995) (l$^{-1}$): 0.3 g NH$_4$Cl, 0.5 g MgCl$_2$.6H$_2$O, 0.1 g CaCl$_2$.2H$_2$O, 0.5 g KCl, 0.83 g sodium acetate trihydrate, 2 g tryptone, 30 g NaCl, 3.3 g PIPES, 1 ml of polyvitamin solution and 0.5 ml of 0.2 wt % resazurin. Along with tryphone and acetate as potential carbon sources for fermentation, yeast extract was also supplied (0.5 wt %-2 g/l) in the absence of elemental sulfur. The medium was maintained under a 100% N$_2$ atmosphere, and after autoclaving at 120° C. for 20 minutes, it was adjusted to the optimal pH of 6 by the addition of 7 wt % K$_2$HPO$_4$ and KH$_2$PO$_4$ solutions. Culture medium was successfully maintained free of contamination throughout the course of the experiment. The pre-inoculum culture grew heterotrophically under elemental sulfur respiration for 16 hours before starting the continuous growth assay.

Cells were stained with 0.1 wt % acridine orange solution and visualized with an Olympus BX 61 microscope with an oil immersion objective (UPlanF1 100/1.3). Scanning electron micrographs were taken using a model JSM-6500F field emission scanning electron microscope (JEOL). The beam was operated at 1 nA and 15 kV. For scanning electron microscopy, cells were collected on polycarbonate RC filters pre-coated with 0.5 nm Iridium to prevent charging under the ion beam (Musat et al., Detecting metabolic activities in single cells, with emphasis on nanoSIMS, *Ferns Microbiol Rev*, 36(2), 486-511, 2012). A final layer of 0.5 nm Iridium was sputtered on the surface of processed filters.

Specific growth rates (h$^{-1}$) were determined by the change/unit of cell concentration as function of time:

$$\mu = \frac{1}{C}\frac{dC}{dt} = \frac{\ln(2)}{t_d}$$

where C is cell density (number of cells/ml) and $t_d$ is the doubling time in hours (h). The rate μ was calculated by the slope of the linear function between the natural logarithm values of cell densities and incubation time.

Dissolved formate concentrations were measured in filtered subsamples (0.2 μm pore-size RC syringe filters) by ion chromatography (Metrohm "MIC-3 Advanced IC", Metrosep A supp 7-250 column) with estimated uncertainties (2σ) of less than 2%.

Statistical Analysis

The statistical analysis was performed utilizing the technical graphic and data analysis software IGOR Pro and Arc 1.06 (http://www.stat.umn.edu/arc) (Cook and Weisberg, *Applied regression including computing and graphics*, 632 pp., Wiley-Interscience, 1999). The error in fit parameters was derived from the covariance matrix as SQRT(cov$_{ii}$), reflecting deviation of 2σ (95.4% confidence interval). 1/(analytical error)$^2$ values were applied as weight (York, Least squares fitting of a straight line with correlated errors, *Earth and Planetary Science Letters*, 5(5), 320-324, 1969). Along with the two-tail probability (p-value), regression models take into consideration the chi-squared ($\chi^2$) distribution of the fitted values to assess the "goodness-of-fit."

TABLE 1

Data from high-pressure continuous culture of *M. piezophila* at 65° C.

| P MPa | Time h | Flow rate ml/min | Agitation rpm | Dilution rate h$^{-1}$ | Residence time h | Cell density cells/ml | [HCOO$^-$]* mM | [CH$_3$COO$^-$]* mM |
|---|---|---|---|---|---|---|---|---|
| 0.1 | 0 | Batch | | | | 1.2 × 10$^6$ | 0 | |
| | 5.2 | | | | | 4 × 10$^5$ | 0.23 | 6.6 |
| | 21.2 | | | | | 2.2 × 10$^6$ | 0.05 | 6.6 |
| | 29.2 | | | | | 2.0 × 10$^6$ | 0.18 | 6.6 |

TABLE 1-continued

Data from high-pressure continuous culture of M. piezophila at 65° C.

| P MPa | Time h | Flow rate ml/min | Agitation rpm | Dilution rate h$^{-1}$ | Residence time h | Cell density cells/ml | [HCOO$^-$]* mM | [CH$_3$COO$^-$]* mM |
|---|---|---|---|---|---|---|---|---|
|  | 46.7 | 2 | 66 | 1.043 | 0.96 | 7.46 × 10$^6$ | 0.07 ± 0.06 | 6.4 ± 0.2 |
|  | 53.2 | 2 | 62 | 1.043 | 0.96 | 2.08 × 10$^6$ | 0.07 ± 0.08 | 6.5 ± 0.1 |
|  | 55.2 | 2 | 55 | 1.043 | 0.96 | 1.56 × 10$^6$ | 0.09 ± 0.08 | 6.6 ± 0.1 |
|  | 70.7 | 0.16 | 62 | 0.083 | 11.98 | 6.2 × 10$^6$ | 0.05 | 6.0 ± 0.3 |
| 10 | 71.7 | 0.16 |  |  |  |  |  |  |
|  | 80.7 | 0.16 | 47 | 0.083 | 11.98 | 4.56 × 10$^6$ | 0.09 ± 0.06 | 6.5 ± 0.2 |
|  | 93.2 | 0.16 | 70 | 0.083 | 11.98 | 7.06 × 10$^6$ | 0.12 ± 0.11 | 6.3 ± 0.3 |
|  | 103.2 | 0.16 | 70 | 0.083 | 11.98 | 3.42 × 10$^6$ | 0.06 ± 0.01 | 6.5 ± 0.1 |
| 20 | 103.2 | 0.16 |  |  |  |  |  |  |
|  | 116.7 | 0.16 | 79 | 0.083 | 76.66 | 7.04 × 10$^6$ | 0.07 ± 0.01 | 6.4 ± 0.1 |
|  | 126.2 | 0.025 | 73 | 0.013 | 76.66 | 3.08 × 10$^6$ | 0.17 ± 0.00 | 6.7 ± 0.0 |
|  | 141.2 | 0.025 | 70 | 0.013 | 76.66 | 7.68 × 10$^6$ | 0.43 ± 0.15 | 6.7 ± 0.1 |
| 30 | 143.2 | 0.025 |  |  |  |  |  |  |
|  | 150.2 | 0.025 | 62 | 0.013 | 76.66 | 3.34 × 10$^6$ | 0.49 ± 0.16 | 6.5 ± 0.2 |
|  | 164.7 | 0.025 | 62 | 0.013 | 76.66 | 4.84 × 10$^6$ | 0.46 ± 0.19 | 7.0 ± 0.3 |
|  | 189.2 | 0.025 | 60 | 0.013 | 76.66 | 1.67 × 10$^7$ | 0.51 ± 0.02 | 6.8 ± 0.1 |
|  | 194.2 | 0.025 | 60 | 0.013 | 76.66 | 2.68 × 10$^6$ | 0.41 ± 0.04 | 6.8 ± 0.0 |
| 40 | 195.2 | 0.025 |  |  |  |  |  |  |
|  | 212.7 | 0.025 | 70 | 0.013 | 76.66 | 4.6 × 10$^6$ | 0.34 ± 0.03 | 6.9 ± 0.8 |
|  | 241.7 | 0.025 |  | 0.013 | 76.66 | 2.96 × 10$^6$ | 0.07 ± 0.10 | 7.7 |
|  | 261.2 | 0.025 | 91 | 0.013 | 76.66 | 1.07 × 10$^7$ | 0.08 ± 0.03 | 8.1 ± 0.2 |
|  | 285.2 | 0.025 | 98 | 0.013 | 76.66 | 1.34 × 10$^7$ | 0.10 ± 0.08 | 7.6 ± 0.4 |
| 30 | 288.7 | 0.025 |  |  |  |  |  |  |
|  | 295.7 | 0.025 | 84 | 0.013 | 76.66 | 8.14 × 10$^6$ | 0.07 ± 0.07 | 7.7 |
|  | 307.7 | 0.025 | 87 | 0.013 | 76.66 | 5.04 × 10$^6$ | 0.08 ± 0.07 | 7.6 |
| 20 | 318.2 |  |  |  |  |  |  |  |
|  | 341.2 | 0.025 | 70 | 0.013 | 76.66 | 1.09 × 10$^7$ | 0.07 ± 0.07 | 7.2 |
| 10 | 341.2 |  |  |  |  |  |  |  |
|  | 357.2 | 0.025 | 80 | 0.013 | 76.66 | 4.68 × 10$^6$ | 0.11 | 8.0 |
|  | 363.7 | 0.025 | 86 | 0.013 | 76.66 | 2.38 × 10$^6$ | 0.07 ± 0.07 | 7.5 |
| 0.1 | 363.7 | 0.025 |  |  |  |  |  |  |
|  | 381.2 | 0.025 | 89 | 0.013 | 76.66 | 2.44 × 10$^6$ | b.d. | 7.6 |

Cell counts were calculated as:

$$\frac{\text{cells}}{\text{ml}} = \frac{\bar{x} \cdot 2.5 \times 10^4}{\text{volume(ml)}} \times 4$$

b.d.: below detection limit; n.a.: not analysed
*Analytical uncertainties correspond to 1σ deviation between replicate measurements.

TABLE 2

Growth parameters of M. piezophila for a range of pressures at 65° C.

| P MPa | Specific growth rate h$^{-1}$ | Doubling time h | Conditions | r$^2$ & p-value for μ |
|---|---|---|---|---|
| 0.1 | 0.05 ± 0.016 | 14.0 ± 4.5 | Batch | 0.76-0.053 |
| 0.1 | −0.19 ± 0.011 |  | 2 ml/min | 0.99-0.036 |
| 10 | (−0.011 ± 0.031)$^\#$ |  | 0.16 ml/min | 0.11-0.783 |
| 20 | (0.009 ± 0.04)$^\#$ |  | 0.16-2 ml/min | 0.05-0.863 |
| 30 | 0.042 ± 0.007 | 16.4 ± 2.7 | 0.025 ml/min | 0.97-0.099 |
| 40 | 0.034 ± 0.016 | 20.5 ± 9.7 | 0.025 ml/min | 0.81-0.283 |

$^\#$Poor quality of fit - calculations for samples collected at 80.7-103.2 h (10 MPa) and 116.7-141.2 h (20 MPa).
Specific growth rates at 30 MPa and 40 MPa were calculated for samples showing evidence of growth. These were collected between 150.2-189.2 and 241.7-285.2 hours at 30 MPa and 40 MPa, respectively. At 0.1 MPa, calculations were conducted for the dataset corresponding to medium flow rates of 2 ml/min (46.7-55.2 h).

It is to be understood that the scope of the present invention is not limited to the specific embodiments described above. The invention may be practiced other than as particularly described and still be within the scope of the accompanying claims.

The invention claimed is:

1. A high pressure bioreactor for the continuous culturing of microorganisms under high pressure, the bioreactor comprising:
   a.) a reactor vessel capable of operating under a pressure between about 5 MPa and about 150 MPa;
   b.) a back-pressure pressure regulator to measure and regulate the pressure of the reactor vessel; and
   c.) a sampler that will not affect the hydrostatic pressure of the microorganisms in the bioreactor while the reactor contents are sampled,
   wherein the bioreactor is gas-tight, the back-pressure regulator is connected to the reactor vessel through connecting tubing, the sampler comprises at least three valves arranged in series with connecting tubing, and one of the at least three valves arranged in series is located between the reactor vessel and the back-pressure regulator.

2. The bioreactor of claim 1 further comprising a pump and valve adapted to add media and cells to the reactor vessel in situ under pressure conditions between about 5 MPa and 150 MPa.

3. The bioreactor of claim 1 further comprising an agitator to homogenize the contents of the reactor vessel.

4. The bioreactor of claim 1 which can operate under aerobic or anaerobic conditions.

5. The bioreactor of claim 1 that can function as a chemostat, retentostat or batch reactor.

6. The bioreactor of claim 1 wherein the valves and connecting tubing are prefilled with deionized water.

7. The bioreactor of claim 1 wherein the reactor vessel is cylindrical.

8. The bioreactor of claim 1, wherein the valves are micrometering valves.

9. A method to allow for the continuous culturing of microorganisms under high pressure, the method comprising:
- a.) providing the bioreactor according to claim 1;
- b.) pre-enriching media solution with dissolved gases in a reservoir;
- c.) filling the bioreactor with growth media at high pressure and at the optimal temperature for growth;
- d.) inoculating the bioreactor with culture;
- e.) operating the bioreactor in the batch mode while the microbial community grows in density to a desired value;
- f.) operating the bioreactor in a continuous mode by adding a continuous flow of media;
- g.) increasing the pressure up to at least about 40 MPa; and
- h.) monitoring the growth by sampling the reactor without affecting the hydrostatic pressure of the microbial community in bioreactor.

10. The method of claim 9 wherein the reactor is sampled using the at least three valves arranged in series.

11. The method of claim 9 wherein the reservoir can withstand at least 60 psi of headspace partial pressure.

12. The method of claim 9 wherein the dissolved gases comprise one or more of $H_2$, $N_2$, $CO_2$ and $O_2$.

13. The method of claim 9 wherein the media solution is pre-heated prior to entering the bioreactor.

14. The method of claim 9 wherein the bioreactor is operated under aerobic or anaerobic conditions.

15. The method of claim 9 wherein sampling does not cause cell lysis of the recovered high-pressure cultures.

16. The method of claim 9 wherein the pressure in the bioreactor is about 150 MPa.

* * * * *